United States Patent [19]

Colley et al.

[11] 4,191,180
[45] Mar. 4, 1980

[54] ENDOTRACHEAL SUPPORT AND STABILIZATION DEVICE

[76] Inventors: Donna J. Colley; Michael L. Easterwood, both of 630 E. 24th St., San Angelo, Tex. 76903

[21] Appl. No.: 889,812

[22] Filed: Mar. 24, 1978

[51] Int. Cl.$^2$ .................... A61M 25/02; A61M 16/00
[52] U.S. Cl. .................. 128/207.17; 128/12; 128/DIG. 26
[58] Field of Search ................... 128/1 R, 12-14, 128/20, 132 R, 188, 185, 206, 208, 348-351, DIG. 26, 303, 303 B

[56] References Cited

U.S. PATENT DOCUMENTS

| 1,021,865 | 4/1912 | Fries | 128/188 |
| 1,319,904 | 10/1919 | Roberts | 128/15 |
| 3,827,433 | 8/1974 | Shannon | 128/351 X |
| 3,946,742 | 3/1976 | Eross | 128/351 |

Primary Examiner—Dalton L. Truluck
Attorney, Agent, or Firm—Daniel Jay Tick

[57] ABSTRACT

An endotracheal support and stabilization device has a generally oval frame framing the face of a user. The frame has a cross-member extending across the face of the user at the level of the nose. The cross-member is movably adjustably mounted on the frame for adjustment to different positions according to different nose positions on different faces. Clamps on the cross-member secure external hoses to the cross-member in a manner whereby tubing from the hoses is maintained inserted into the nostrils of the user without pressure on the nose. A fastener is affixed to the frame and extendable around the back of the user's head for releasably supporting the frame in position framing the user's face with the cross-member extending across the user's nose.

5 Claims, 5 Drawing Figures

ENDOTRACHEAL SUPPORT AND STABILIZATION DEVICE

BACKGROUND OF THE INVENTION

The present invention relates to an endotracheal support and stabilization device. More particularly, the invention relates to an endotracheal support and stabilization device for a person.

Endotracheal supports of the type described herein are disclosed in the following United States patents. U.S. Pat. No. 3,713,448, issued Jan. 30, 1973 to Arrott, U.S. Pat. No. 3,827,433, issued Aug. 6, 1974 to Shannon, U.S. Pat. No. 3,927,676, issued Dec. 23, 1975 to Schultz, U.S. Pat. No. 3,946,742, issued Mar. 30, 1976 to Eross, U.S. Pat. No. 3,993,081, issued Nov. 23, 1976 to Cussell and U.S. Pat. No. 4,018,221, issued Apr. 19, 1977 to Rennie.

Objects of the invention are to provide an endotracheal support and stabilization device of simple structure, which is inexpensive in manufacture, used with facility, convenience and safety on people of any age, and especially infants of a young age such as neonates, and functions efficiently, effectively and reliably to maintain tubing in the nostrils of the patient without pressure on the nose or head thereby avoiding problems with nasal tissues and malformation of the skull of newly born infants.

BRIEF DESCRIPTION OF THE DRAWINGS

In order that the invention may be readily carried into effect, it will now be described with reference to the accompanying drawings, wherein.

DETAILED DESCRIPTION OF THE INVENTION

Figure 1:
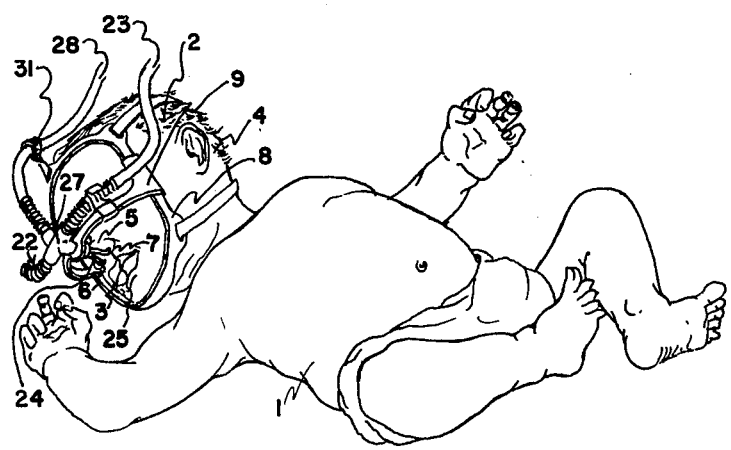
FIG. 1 is a perspective view of an embodiment of the endotracheal support and stabilization device of the invention in use.

The endotracheal support and stabilization device of the invention is for a person 1, and especially an infant, as shown in FIG. 1, having a head 2 with a face 3 in front of the head and a back 4 (FIG. 1). The face 3 has a nose 5 with nostrils 6 and 7 (FIG. 1).

Figure 2:
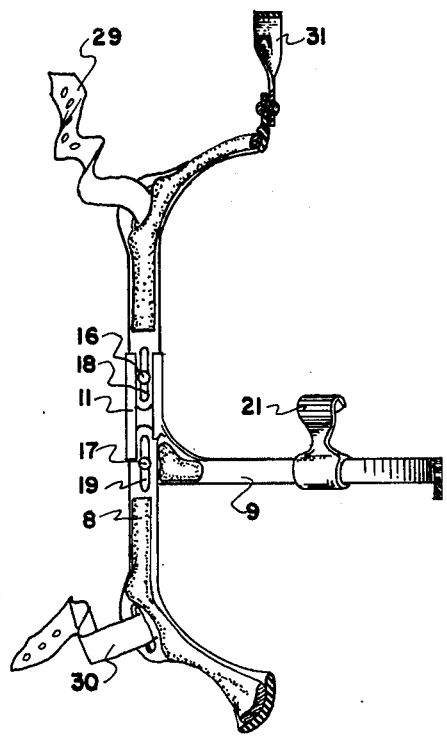
FIG. 2 is a view, on an enlarged scale, partly cutaway, and partly in section, of part of the embodiment of FIG. 1.
Figure 3:
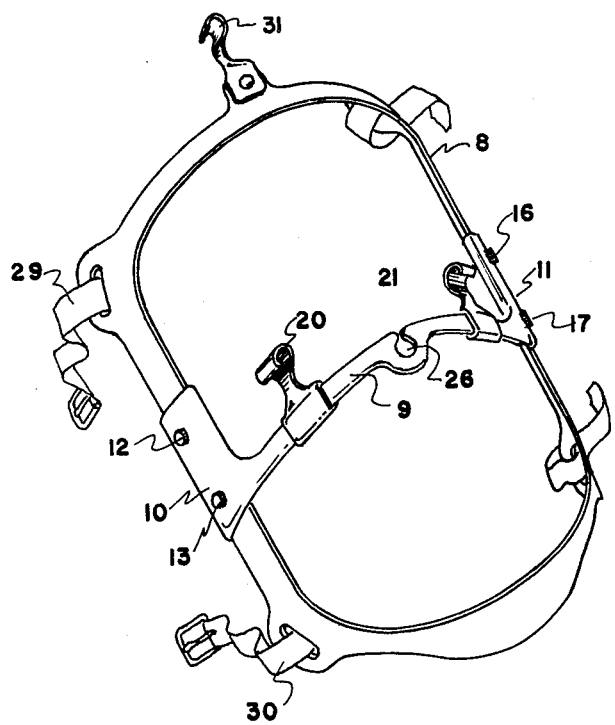
FIG. 3 is a perspective view, on an enlarged scale, of the embodiment of FIG. 1.
Figure 5:
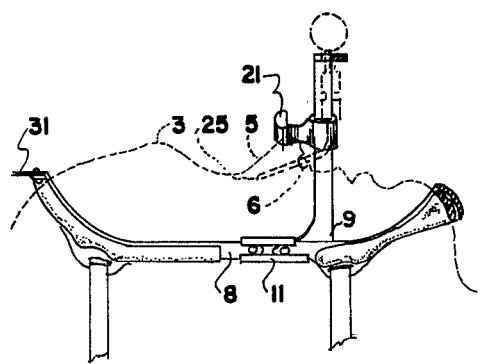
FIG. 5 is a side view, partly cutaway and partly in section, of the embodiment of FIG. 1, in use.
Figure 4:
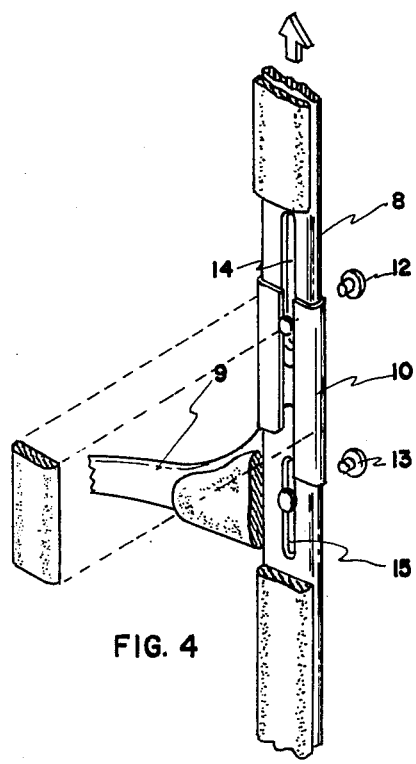
FIG. 4 is a view, on an enlarged scale, partly cutaway and partly in section, of part of the frame of the endotracheal support and stabilization device of the invention.

The endotracheal support and stabilization device of the invention comprises a generally oval frame 8 framing the face 3 of the user 1. The frame 8 has a cross-member 9 (FIGS. 1 to 5) extending across the face 3 of the user 1 at substantially the level of the nose 5, as shown in FIGS. 1 and 5. The cross-member 9 is movably adjustable mounted on the frame 8 for adjustment to different positions according to different nose positions on different faces. Thus, for example, the cross-member 9 is slidably mounted at each of its opposite ends, on the frame 8, via a pair of brackets 10 and 11, as shown in FIG. 3. The cross-member 9 is secured in a selected position via bolts 12 and 13 passing through corresponding slots 14 and 15 on one side of the frame 8, as shown in FIGS. 3 and 4, the bolts 16 and 17 passing through corresponding slots 18 and 19 formed through the other side of said frame, as shown in FIG. 2.

A pair of clamps 20 and 21 are provided on the cross-member 9, as shown in FIG. 3, for securing external hoses 22 and 23 to the cross-member, as shown in FIG. 1, in a manner whereby tubing 24 and 25 from said hoses is maintained inserted into the nostrils 6 and 7 of the user 1 without pressure on the nose or any of the nasal or facial tissues. The cross-member 9 has a circular slot 26 formed therethrough at the center thereof, as shown in FIG. 3, for accommodating a T-joint 27, as shown in FIG. 1, to enable both hoses 22 and 23 to be secured thereon, at a common point with a third hose 28, as shown in FIG. 1.

Fastening devices are affixed to the frame 8 and extendable around the back 4 of the user's head 2 for releasably supporting said frame in position, framing the user's face 3 with the cross-member 9 extending across the user's nose 5, just beneath such nose, as shown in FIGS. 1 and 5. The fastening devices comprise two pairs of straps 29 and 30 (FIGS. 2 and 3) which are selectively buckled to fit around the user's head without discomfort or malformation of the head. The sets of straps 29 and 30 may be elastic, if desired.

A third clamp 31 (FIGS. 1 to 3 and 5) is provided at the center of the top of the frame 8 for securing the third hose 28 to said frame, as shown in FIG. 1.

While the invention has been described by means of a specific example and in a specific embodiment, we do not wish to be limited thereto, for obvious modifications will occur to those skilled in the art without departing from the spirit and scope of the invention.

We claim:

1. An endotracheal support and stabilization device for a person having a head with a face in front of the head and a back, the face having a forehead, a nose with nostrils and a chin, said endotracheal support and stabilization device comprising a generally oval frame framing the face of a user, said frame having spaced opposite upper and lower parts and spaced opposite side parts substantially parallel to each other and a cross-member mounted transversely on the side parts of said frame and extending across the face of the user substantially perpendicular to said side parts at substantially the level of the nose, said cross-member being slidably mounted on said side parts of said frame for adjustment to different positions from said upper and lower parts of said frame according to different nose positions on different faces;

clamp means on said cross-member for securing external hoses to said cross-member in a manner whereby tubing from said hoses is maintained inserted into the nostrils of the user free from pressure on the nose; and fastening means affixed to said frame and extendable around the back of the user's head for releasably supporting the frame in position framing the user's face with said cross-member extending across the user's nose, the upper part in the area of the forehead of the user and the lower part in the area of the chin of the user.

2. An endotracheal support and stabilization device as claimed in claim 1, wherein each of the side parts of said frame has slots formed therethrough, and further comprising a plurality of bolts passing through said slots and threadedly coupled to said cross-member for slidably securing said cross-member in said slots.

3. An endotracheal support and stabilization device as claimed in claim 2, wherein said cross-member has a circular slot formed therethrough equidistantly from said side parts of said frame, and further comprising a T-joint accommodatable in the circular slot for securing a pair of hoses at a common point with a third hose.

4. An endotracheal support and stabilization device as claimed in claim 3, wherein said clamp means comprises a pair of clamps each provided on said cross-member between said circular slot and a corresponding one of said side parts of said frame and a third clamp provided on said top part of said frame.

5. An endotracheal support and stabilization device as claimed in claim 3, wherein said fastening means comprises two pairs of straps selectively buckled to fit around the head of the user.

* * * * *